United States Patent [19]
Sapp et al.

[11] Patent Number: 5,430,541
[45] Date of Patent: Jul. 4, 1995

[54] HIGH EFFICIENCY FLUORESCENCE FLOW CELL FOR CAPILLARY LIQUID CHROMATOGRAPHY OR CAPILLARY ELECTROPHORESIS

[75] Inventors: Edwin Sapp, Hillsdale, N.J.; Robert Weinberger, Chappaqua, N.Y.

[73] Assignee: Applied Biosystems Inc., Foster City, Calif.

[21] Appl. No.: 3,351

[22] Filed: Jan. 12, 1993

[51] Int. Cl.⁶ .......................................... G01N 21/05
[52] U.S. Cl. .................................. 356/246; 356/318
[58] Field of Search ................ 356/246, 317, 318, 417

[56] References Cited

U.S. PATENT DOCUMENTS

| | | | |
|---|---|---|---|
| 4,088,407 | 5/1978 | Schoeffel et al. | 356/246 |
| 4,199,686 | 4/1980 | Brunsting et al. | 250/459 |
| 4,273,443 | 6/1981 | Hogg | 356/343 |
| 4,548,498 | 10/1985 | Folestad et al. | 356/318 |
| 4,675,300 | 6/1987 | Zare et al. | 436/172 |

OTHER PUBLICATIONS

Stephen E. Moring et al, *Analytical Aspects of an Automated Capillary Electrophoresis System*, LC-GC, vol. 8, No. 1.

Michael Albin et al, *Fluorescence Detection in Capillary Electrophoresis: Evaluation of Derivatizing Reagents and Techniques*, Analytical Chemistry, 1991, p. 63.

Alfredo E. Bruno et al, *On-Column Capillary Flow Cell Utilizing Optical Waveguides for Chromatographic Applications*, Anal. Chem., 1989, 61, pp. 876-883.

*Primary Examiner*—Richard A. Rosenberger
*Attorney, Agent, or Firm*—John A. Frazzini

[57] ABSTRACT

A fluorescence flow cell having a capillary through which a sample fluid is moved, an optical source that directs an exposing beam of light through the sample fluid, a collector that collects fluorescent light from the exposed region of the sample and directs such collected light to a detector. A beam blocker prevents light that is scattered by the capillary walls from reaching the detector, thereby improving the signal-to-noise ratio of the system. The beam blocker also has a pair of legs that prevent the sample fluid from being exposed by either the exposing light or the collected light outside of the exposing region. The structure of the components enables the various components to be quickly and accurately assembled and enables easy replacement of the capillary.

10 Claims, 1 Drawing Sheet

HIGH EFFICIENCY FLUORESCENCE FLOW CELL FOR CAPILLARY LIQUID CHROMATOGRAPHY OR CAPILLARY ELECTROPHORESIS

FIELD OF THE INVENTION

This invention relates in general to chromatographic methods and apparatus for chemical analysis and relates more particularly to a fluorescence capillary flow cell having an improved signal-to-noise ratio.

CONVENTION REGARDING REFERENCE NUMERALS

In the figures, each element indicated by a reference numeral will be indicated by the same reference numeral in every figure in which that element appears. The first digit of any reference numeral indicates the first figure in which its associated element is presented.

BACKGROUND OF THE INVENTION

Chromatographic methods are commonly used to separate a mixture into various components, so that these components can be identified and quantified. In one class of chromatographic methods, mixtures are transmitted along a separation column through which the various components migrate at different flow velocities. Such techniques are applied to gaseous samples as well as to liquid samples. These techniques are now widely utilized in chemical, biological and medical applications.

A variety of mechanisms are utilized to produce the desired separation between the components of the mixture. In one class of systems, the wall of the tube through which the mixture flows is coated with a material that exhibits different affinities for different components of the mixture. The speed of migration along the channel is greater for components exhibiting a weaker affinity for the wall, thereby producing a separation of mixture components according to their affinity for the coated wall.

In another class of systems, the column is packed with a material, such as a gel, that provides the differential interaction with the components of the mixture. The packing functions as a sieve that physically retards the flow of larger molecules more than it retards the flow of smaller molecules. In addition, the surface of the packing can contain chemical groups that control the affinity between the packing and various components of the mixture. Therefore, the wide range of choices of pore size and surface groups makes packings, such as gels, a very flexible medium for separating the components of the mixture. The sample fluid can be forced through this packing by a number of techniques, such as a pressure difference between the inlet and outlet ends of the capillary (also referred to herein as a "column") and/or the use of capillary electrophoresis to drive sample ions through the packing.

These separation columns typically pass the sample solution past a detector that measures some physical property of the components, such as the absorbance spectrum, the fluorescence spectrum, the refractive index or the electrical conductivity of the sample solution. In each of the first three of these particular cases, an optical beam is passed through the sample. For the case of absorbance measurements, a detector is positioned along a straight line through the optical source and the separation column to receive the optical beam after it passes through the sample. Fluorescence detection exhibits the advantages of superior selectivity and sensitivity in detecting many compounds.

For the case of fluorescence measurements, the location of the detector is determined by considerations of the signal-to-noise ratio of the output of the detector. As taught in U.S. Pat. No. 4,548,498 entitled *Laser Induced Fluorescence Detection In Modem Liquid Chromatography With Conventional And Micro Columns* issued to Folestad, et al on Oct. 22, 1985, the incident beam of light is typically perpendicular to the axis of the capillary and therefore scatters off of the wall of the capillary into a plane oriented perpendicular to the axis of the capillary and passing through the point of the capillary illuminated by the incident beam of light. To avoid such scattered light in the case of fluorescent light detection, the detector is positioned outside of this plane and oriented to receive light from the sample along a direction at 30° with respect to the plane of scattered light. U.S. Pat. No. 4,675,300 entitled *Laser Excitation Fluorescence Detection Electrokinetic Separation* issued to Zare, et al on Jun. 23, 1987 teaches that the use of a coherent light has the advantage of reducing the Raman and Rayleigh scattering components of the scattered light.

Conventional flowcells for fluorescence detectors for capillary liquid chromatography often use a lens to focus excitation light onto the liquid column and often use a lens to focus fluorescent light onto the detector. In the capillary flowcell presented in the article *On-Column Capillary Flow Cell Utilizing Optical Waveguides For Chromatographic Applications* by Alfredo E. Bruno, et al, Anal. Chem. 1989, 61, p. 876–883 optical fibers are utilized to carry incoherent light to the flowcell and are also utilized to transmit fluorescent light from the flowcell to a detector.

This article further teaches that optical fibers are as efficient as laser sources in directing the exposing light through the bore of the capillary to the capillary flowcell. For a capillary of specified inner and outer diameters, a ray path calculation is presented that enables a determination of the maximum diameter of the source optical fiber and the minimum diameter of the collecting optical fiber needed to pass substantially all of the source light through the bore of the capillary to the collecting optical fiber. An analysis of the distribution of scattered light and the fraction of incident light that actually passes through the bore of the capillary is also presented in this article. Because there is no focussing of the light from the capillary onto the collecting optical fiber, the collection efficiency of the collecting optical fiber is limited by its acceptance angle and the spacing between the capillary input end of this collecting optical fiber. Typically, each of these fluorescent systems collects less than one-eighth of the fluorescent light emitted from that system.

U.S. Pat. No. 4,199,686 entitled *Dark Field Illuminator And Collector Apparatus And Method* issued to Brunstig, et al on Apr. 22, 1980 and U.S. Pat. No. 4,273,443 entitled *Method And Apparatus For Measurement Of Reradiation In Particle Flow Cell Systems* issued to Walter P. Hogg on Jun. 16, 1981 present optical sections of a device for counting particles, such as biological cells. Although this optical section is efficient at collecting fluorescent light emitted by the particles exposed by the incident light, it just as efficiently collects the light scattered by these particles as well as the light that passes through the particle stream without being scattered or absorbed by the particles. Therefore, some mechanism, such as a dichroic filter or a Fresnel prism, is included to deflect the nonfluorescent portion of the light focussed by the optical section onto the detector. The need for this mechanism increases the complexity and cost of this system. Furthermore, to the extent that this mechanism is not 100% efficient in discriminating against such nonfluorescent portion of the collected light, this structure will exhibit a reduced signal-to-noise ratio.

U.S. Pat. No. 4,088,407 entitled *High Pressure Fluorescence Flow-Through Cuvette* issued to Dietmar M. Schoeffel, et al on May 9, 1978, presents a cuvette for liquid chromatographic analysis. A collector, formed as a reflective coating on a surface that is parabolic, circular or elliptical surface or revolution, redirects part of the fluorescent light onto a detector. Because of the large size of the chamber into which the sample liquid is directed for fluorescent excitation, this structure is unsuitable for use with capillary-based systems such as capillary liquid chromatography and capillary electrophoresis, because it would introduce a completely unacceptable amount of band broadening into the chromatic separation process. Because the specification lacks any dimensional details regarding the collector and the width of the beam of exposing light, it is impossible to determine the efficiency of this structure for collecting the fluorescent light from the exposing region of the sample liquid.

Because the use of small diameter bore capillaries improves the separation between the components of a sample, capillary liquid chromatography uses columns with very small internal diameters (typically 5 to 300 microns). Because of this, only a very small quantity of sample (on the order of 1-2 nanoliters) is exposed at any given time during a measurement. Therefore, the signal to noise ratio (referred to as the "S/N ratio") for such systems is very dependent on: the fraction of fluorescent light from the sample that is actually collected by a system detector; and the amount of stray light that reaches the detector. A major limitation in the use of fluorescence detection has been the achievable signal to noise ratio.

The S/N ratio has been improved by use of stronger light sources and/or coherent light sources in which the energy is concentrated at a wavelength that is particularly efficient at producing fluorescence. This improvement therefore arises from an increased amplitude of the signal. However, part of the noise component, such as scattered light, is proportional to the intensity of the exposing light. Therefore, when this portion of the noise is a significant fraction of the total noise, it is important to minimize such component. It is therefore very important to utilize a structure that prevents substantially all stray light from reaching the detector, so that the noise component is minimized. This means that care must be taken to minimize the amount of scattered light that is produced and to ensure that substantially none of this scattered light reaches the detector. It is also important to ensure that a very high fraction of the fluorescent light emitted by the sample reaches the detector, so that the signal component of the detector output is substantially maximized.

SUMMARY OF THE INVENTION

A fluorescence flowcell is presented that is very efficient at collecting fluorescent light emitted from a sample transmitted through a capillary. This flowcell is particularly useful in capillary liquid chromatography ("LC") and capillary electrophoresis ("CE"), but is applicable to any fluorescent measurement in which the sample is separated in a capillary.

In order to maintain chromatographic integrity, it is preferred that detection be done "on-column" (i.e., the collected fluorescent light is emitted by fluid within the column or within a column extender) to avoid the dispersion that can occur with "off-column" (i.e., the collected light is emitted by the fluid after leaving the separation column) detection. However, off-column detection can also be utilized in this flowcell. Such off-column detection can be achieved, for example, by a free falling jet at an outlet of the capillary, by sheathing flow at an outlet of the capillary or by directing the exposing light through a capillary gap junction, as taught in the article by Michael Albin, et al entitled *Fluorescence Detection in Capillary Electrophoresis: Evaluation of Derivatizing Reagents and Techniques*, Analytical Chemistry, 1991, vol. 63, p. 417–422. An electric field produced across the capillary gap junction substantially eliminates band broadening as a sample passes across this gap junction. In all of these cases (e.g., flow of liquid within the column, flow within a capillary extender, flow across a capillary gap junction, flow within a free falling jet, within a sheathing flow or any other flow that produces a flow comparable to that within a capillary will be referred to herein as a "capillary stream" of liquid.

The flowcell includes a fluorescent light collector that subtends a solid angle of approximately $2\pi$ steradians or more and that redirects fluorescent light within this solid angle to a detector. Because fluorescent radiation is substantially uniformly distributed over a complete spherical solid angle, this collector directs approximately half of the fluorescent light to the detector. This collector preferably has the form of a surface of revolution having a transverse cross-section selected to direct the fluorescent light incident thereon onto a detector. The symmetry of this structure makes it easier to manufacture than embodiments that do not have this symmetry. However, systems that approximate this symmetry will exhibit substantially the same improved signal to noise ratio. This transverse cross-section is preferably a conic section such as a half-ellipse, parabola or semicircle. This collector preferably has the form of a reflective coating on the outer surface of a solid block of transparent material, because this produces a rugged collector that is easily manufactured and assembled to the other components in this flow cell.

An optical source directs a beam of exposing light onto a region (the "exposing region") of the capillary stream that preferably is adjacent to or intersects the rotational axis of the collector, so that the collector and the distribution of fluorescent light have a common symmetry axis. This produces a beam of fluorescent light that also exhibits the same rotational symmetry. In on-column embodiments, the exposing region is located at a point where a protective coating has been removed from the capillary to make it transparent in the that region or is located of a transparent capillary extender.

An opaque beam blocker, located between the capillary and the collector, is included to block scattered light from reaching the collector. This greatly reduces the noise component of the output signal, thereby providing a significant increase in the signal-to-noise ratio compared to other fluorescence detection systems. In the on-column measurement embodiments, the dominant portion of the scattered light arises from the scatter of light off of the outer and inner surfaces of the of the capillary. In the off-column detection embodiments, a significant portion of the scattered light arises from the scatter of light off of the cylindrical surface of the sample. In those embodiments in which the exposing light is in the form of a beam directed perpendicular to the axis of the capillary, this scattered light is strongly peaked in a planar, disk-shaped region having its normal parallel to the axis of the capillary. In embodiments in which the exposing light is not perpendicular to the axis of the capillary, the scattered light is also scattered primarily into a disk-shaped region. In such embodiments, the portion of the beam blocker that blocks the scattered light will typically be a narrow, curved region.

This beam blocker can also include a portion that is positioned between the collector and the capillary to prevent any light, reflected from the collector, from being incident onto the capillary outside of the desired exposing region. In the preferred embodiment, the exposing light is perpendicular to the capillary and the beam blocker has the form of a cross having a hole at the junction of the two legs of this cross.

In the preferred embodiment, the collector has the shape of a surface of revolution generated by a circular arc of angular span less than $\pi$. The center of the planar, circular bottom edge of this is centered over the exposing region and is adjacent to the capillary, so that this collector collects almost half of the fluorescent light emitted from the exposing region. This choice is advantageous, because it is an inexpensive shape to manufacture and because this reflects fluorescent light from the exposing region into a converging or collimated beam of light that is enough larger in diameter than the widths of the legs of the beam blocker that only a small fraction of this fluorescent light reflected by the collector is absorbed by the beam blocker.

Although the source of the exposing light can be located inside of the collector, it is convenient to mount this source outside of the collector and to direct the beam of exposing light either along or approximately along the axis of symmetry of the collector. This has the advantage of placing this source in a location that makes it easy to replace and exposes the capillary from the side facing the collector so that the greatest fluorescence per unit volume in the sample is adjacent to the side of the capillary facing the collector.

DESCRIPTION OF THE PREFERRED EMBODIMENT

Figure 1:
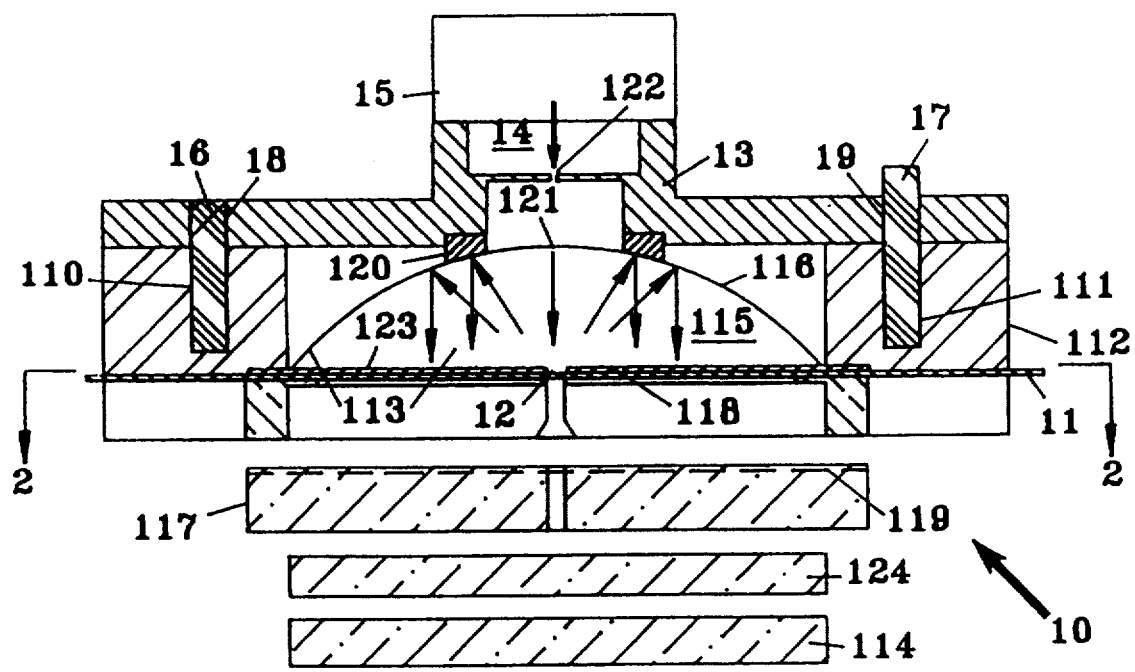
FIG. 1 is a side cross-sectional view of a high efficiency fluorescence flow cell for capillary liquid chromatography or capillary electrophoresis.
Figure 2:
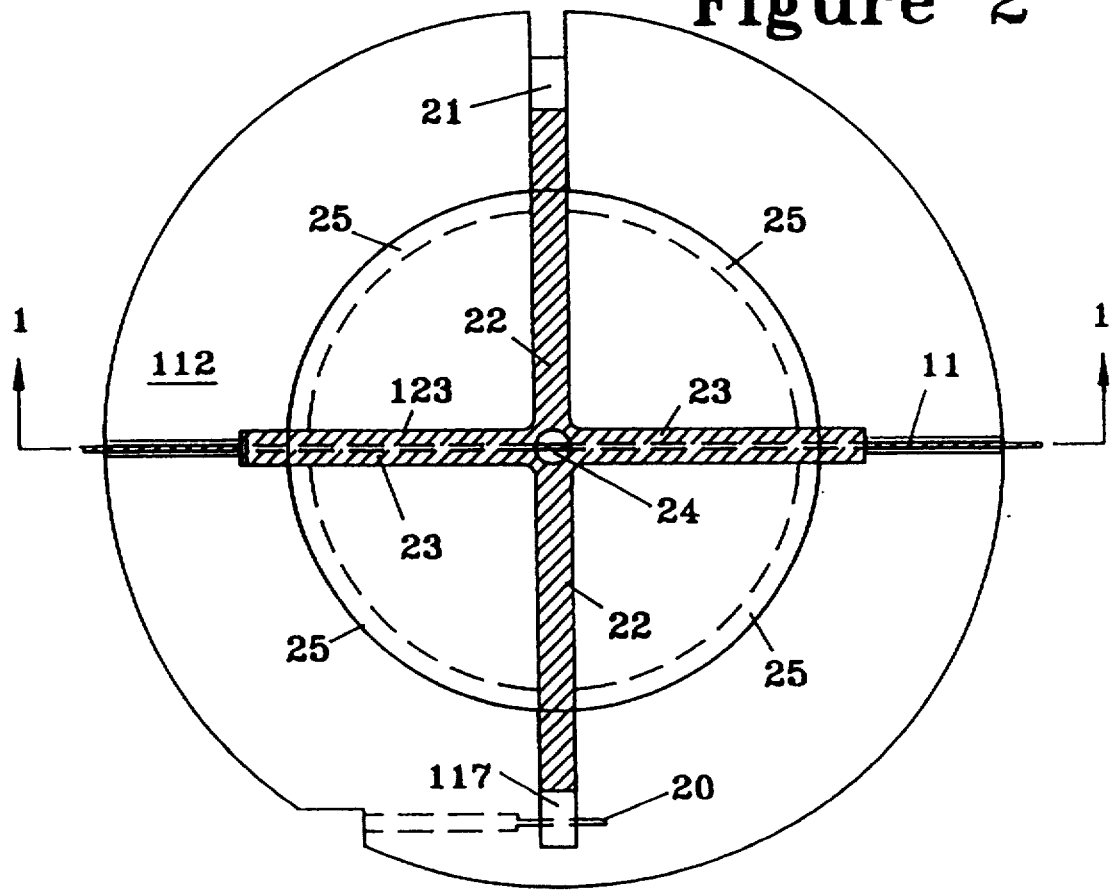
FIG. 2 is a bottom cross-sectional view of the flow cell of FIG. 1.

FIGS. 1 and 2 are, respectively, side and bottom cross-sectional views of a high efficiency fluorescence flow cell 10 for capillary chromatography. As is illustrated in FIG. 1, the solvent mobile phase and a sample analyte are transmitted through a capillary 11 having an outer diameter typically on the order of 50 to 1000 microns and an inner diameter on the order of 5 to 300 microns. The capillary can contain packed compounds or gels to aid in this separation or it can contain no packing medium (i.e., be used "open tubular" with a coated or uncoated interior wall). Flow of fluid through the capillary can be produced by a number of mechanisms, including hydrodynamic, electrodynamic (CE), gravitational and/or vacuum means.

Capillaries are typically coated with a protective polyimide coating that provides physical protection of the capillary against scratching and breakage. In the preferred on-column detection embodiment, this coating is removed in a exposing region 12 of length on the order of a few millimeters to enable exposing light to reach the sample and to enable fluorescent light to exit from the capillary. The volume of the exposing region is typically on the order of 1 to 2 nanoliters.

Flowcell 10 includes an optical source mount 13 to which an optical source 15 is mounted. Source 15 can be a broad or narrow wavelength band of optical radiation and can be a coherent or incoherent source. Such a source includes focussing optics to focus the beam onto the inner diameter of the transparent portion of capillary 11. Typical sources include a deuterium lamp, a laser, a xenon arc lamp (continuous or pulsed) or a tungsten halogen lamp with a monochromator and/or optical filters to spectrally define the beam. This light incident on the capillary is selected to stimulate fluorescent emission from the solutes of interest.

A pair of pins 16 and 17 are each press-fit through an associated opening 18 and 19 in optical source mount 13 into an associated one of cylindrical recesses 110 and 111 in a housing 112 to align and attach the optical source mount to the housing. The flowcell includes a collector 113 that is utilized to collect fluorescent light emitted from a sample within capillary 11 and to direct it onto a detector such as photomultiplier 114. Collector 113 consists of a solid block 115 of translucent (preferably, transparent) material, such as quartz glass, on a curved top surface of which is coated a reflective coating 116, such as silver or aluminum.

A cross-shaped retaining bar 117 is adapted to clamp the capillary into the flowcell. Although this bar is shown displaced vertically below the housing 112, as illustrated in FIG. 2, it is actually pivotally attached by a retaining pin 20, so that it can be easily rotated away from the capillary to provide an easy mechanism for replacing the capillary. This bar is of an opaque material, such as aluminum, so that it also functions to block that portion of the exposing light that passes through the capillary toward the detector. This reduces the noise component of the output signal from the detector, thereby improving the signal-to-noise ratio of this device.

The capillary fits snugly within a channel formed by a bottom surface 118 of block 115 and a groove 119 in a top surface of retaining bar 117. As illustrated in FIG. 2, retaining bar 117 is attached to housing 112 by a retaining pin 20 about which retaining bar 117 can rotate. A latch 21 is utilized to clamp the retaining bar against the capillary. As illustrated in FIG. 1, a ring-shaped pressure pad 120 of a resilient material presses against the curved top surface of block 115 and produces a snug fit between mount 13, pressure pad 120, block 115 and a ledge 25 shown in FIG. 2. A snug fit is produced between retaining bar 117, capillary 11, beam blocker 123 and the bottom surface 118 of collector 113, so that the collector and capillary are firmly held in place. This also presses the capillary within groove 119 in the retaining bar so that the capillary is accurately positioned within flow cell 10.

A region 121 of reflective coating 116 is removed, so that light can pass from optical source 15 through an aperture 122 in the optical source mount and through region 121 to expose the capillary in the exposing region 12 in which the protective capillary coating has been removed. Aperture 122 defines the lateral size of the beam passing through this aperture. A recess 14 in the optical source mount 15 is included so that the thin plate containing this aperture is protected from damage during assembly of this device. An opaque beam blocker 123, located between capillary 11 and the bottom surface 118 of block 115 has a first pair of legs 22 that prevent light scattered from the capillary from reaching detector 114, thereby greatly improving the signal-to-noise ratio of this system. Beam blocker 123 also includes a second pair of legs 23 that prevent light reflected by collector 113 from interacting with the fluid within capillary 11. This prevents unwanted excitation outside of exposing region 12. This is important because the capillary functions to separate spatially different components of the sample. Therefore, if the capillary is exposed outside of a narrow exposing region, then the spectral data will be a sum of data from a range of contiguous spatially separated components of the sample, thereby degrading the spectral data. A wavelength selective element, such as filter 124 is included in the optical path between collector 113 and detector 114 to pass substantially only those wave-lengths that are contained in the fluorescence light emitted by the sample of interest.

In an alternate embodiment, legs 22 could be eliminated, because retainer bar 117 can be used to block the scattered light. In another embodiment, legs 23 can be replaced by a pair of opaque sleeves that encircle capillary 11 in the regions that are shielded by legs 23 in the embodiment of FIGS. 1 and 2. However, a disadvantage of this latter structure is that the capillary must be threaded through such sleeves, which is a more difficult and time-consuming operation than positioning the beam blocker such that legs 23 shield capillary 11 on each side of the exposing regions. A hole 24 in the intersection of these two pairs of legs enables the exposing light to impinge onto the capillary in the exposing region and also defines the diameter of the exposing region.

Following are four alternate embodiments of both on-column and off-column detection. In a first alternate embodiment, a transparent capillary extender is attached to the capillary and positioned within this flow cell such that the exposing and fluorescent light pass through the wall of this capillary extender. Because the capillary extender functions as part of the capillary, in the claims, the word "capillary" includes the capillary and any capillary extender attached thereto to enable light to be transmitted to and from the sample.

In a second alternate embodiment, the sample is allowed to exit from the capillary as a free-falling jet of liquid through which the exposing light is directed adjacent to the exit end of the capillary. In this embodiment, the flowcell is oriented such that the capillary is substantially vertical so that the sample liquid will drop by gravity along the axis of the capillary. In a third alternate embodiment, a sheathing flow at the output of the capillary produces an exposing region of adjacent to the output end of the capillary and having a diameter substantially equal to the inner diameter of the capillary.

In a fourth alternate embodiment, capillary 11 includes a capillary gap junction in exposing region 12. The structure of capillary gap junctions is presented in the article by Michael Albin, et al entitled *Fluorescence Detection in Capillary Electrophoresis: Evaluation of Derivatizing Reagents and Techniques*, Analytical Chemistry, 1991, Vol. 63, p. 417–422. In this system, a capillary gap junction is included across which is produced an electric field that substantially eliminates band broadening as a sample passes across this gap junction. Each end of the capillary is inserted into an associated vessel containing the electrolyte that is moved through the capillary. The electric field across the gap is just a portion of the electric field used to drive the sample through the capillary by capillary electrophoresis. This electric field is produced by a voltage source, a pair of electrodes, each of which is inserted into the sample solution in an associated one of these two vessels. This gap provides an off-column region through which an optical beam can be directed to induce fluorescence in the sample.

We claim:

1. A fluorescence flow cell comprising:
   a capillary through which a sample fluid is to be transported;
   an optical source that directs an exposing beam onto an exposing region of the capillary to induce fluorescence from said sample fluid;
   an optical detector;
   a collector, to which said optical source is attached, that directs fluorescent light from said sample fluid to said detector, said optical source being attached to said collector;
   a groove, in a bottom surface of said collector, into which said capillary is pressed to align said capillary into said exposing beam; and
   an opaque beam blocker that blocks light that scatters from said exposing beam off of said capillary toward said detector.

2. A fluorescence flow cell as in claim 1 wherein said exposing beam is substantially perpendicular, at said exposing region, to an axis of said capillary.

3. A fluorescence flow cell as in claim 1 wherein said beam blocker blocks all light to said capillary from said exposing beam and from said collector, except within said exposing region, whereby resolution is not degraded by exposure of said sample fluid outside of said exposing region and whereby fluorescent light, directed by said collector along directions that would illuminate the capillary, is prevented from reaching said capillary.

4. A fluorescence flow cell as in claim 3 wherein:
   said exposing beam is substantially perpendicular, at said exposing region, to an axis of said capillary;
   said beam blocker has the shape of a cross having a hole in a center of said cross; and
   said cross is positioned and oriented such that a first pair of legs of this cross are positioned to block scattered light from reaching the detector and a second pair of legs of this cross are aligned with the capillary to block light from said collector from illuminating the capillary.

5. A fluorescence flow cell as in claim 1 wherein said collector collects fluorescent light over a solid angle of approximately $2\pi$ steradians.

6. A fluorescence flow cell as in claim 1 wherein said collector has a reflective surface having the form of a portion of a conic section.

7. A fluorescence flow cell as in claim 1 wherein said collector comprises:

a transparent block having a curved top surface that is coated with a reflective coating, the shape of this curved top surface being such that fluorescent light from said exposing region is directed toward said detector.

8. A fluorescence flow cell as in claim 7 wherein said transparent block has a flat bottom surface, said flow cell further comprising:
a retainer that presses the capillary into said groove in said flat bottom surface and aligns said capillary to intersect said exposing region, whereby said capillary is easily and accurately mounted to intersect said exposing beam.

9. A fluorescence flow cell as in claim 8 wherein said retainer is opaque and is positioned to block exposing light from passing through the capillary to said detector.

10. A fluorescence flow cell as in claim 8 wherein:
said optical source is mounted to said collector such that this source directs said exposing light through an opening in said reflective coating, through said transparent block and exposing region toward said detector; and
said retainer blocks unscattered exposing light from reaching said detector.

* * * * *